(12) United States Patent
Pierce et al.

(10) Patent No.: US 7,609,074 B2
(45) Date of Patent: Oct. 27, 2009

(54) ELECTRONIC MOISTURE TESTER

(75) Inventors: Brian N. Pierce, Chico, CA (US); Orion Davies, Chico, CA (US); Michael Gildemeister, Sutter, CA (US)

(73) Assignee: Sunsweet Growers, Inc., Yuba City, CA (US)

( * ) Notice: Subject to any disclaimer, the term of this patent is extended or adjusted under 35 U.S.C. 154(b) by 745 days.

(21) Appl. No.: 11/066,850

(22) Filed: Feb. 24, 2005

(65) Prior Publication Data

US 2006/0188616 A1    Aug. 24, 2006

(51) Int. Cl.
*G01R 27/08*    (2006.01)
*G01R 27/26*    (2006.01)
*G01N 25/56*    (2006.01)

(52) U.S. Cl. .............................. 324/694; 324/664; 73/73

(58) Field of Classification Search ................ 324/694, 324/693, 691, 649, 600, 664, 689, 441, 449; 73/24.04, 25.04, 29.01, 73, 335.06
See application file for complete search history.

(56) References Cited

U.S. PATENT DOCUMENTS

| | | | |
|---|---|---|---|
| 3,005,154 A | 10/1961 | Moore et al. | |
| 3,467,860 A | 9/1969 | Trischberger | |
| 3,966,973 A | 6/1976 | Henry et al. | |
| 4,580,233 A | 4/1986 | Parker et al. | |
| 4,584,522 A | 4/1986 | Varela | |
| 4,616,425 A | 10/1986 | Burns | |
| 4,762,060 A * | 8/1988 | Santa Cruz | 99/483 |
| 5,167,769 A * | 12/1992 | Jack et al. | 162/238 |
| 5,514,973 A | 5/1996 | Byler et al. | |
| 6,053,873 A * | 4/2000 | Govari et al. | 600/505 |
| 6,366,099 B1 | 4/2002 | Reddi | |
| 6,391,024 B1 * | 5/2002 | Sun et al. | 606/34 |
| 6,420,882 B1 | 7/2002 | Engebretsen et al. | |
| 6,437,582 B1 | 8/2002 | Rode et al. | |
| 6,489,784 B2 | 12/2002 | Adams et al. | |
| 6,648,883 B2 * | 11/2003 | Francischelli et al. | 606/41 |
| 6,747,461 B2 | 6/2004 | Corak et al. | |
| 6,747,463 B2 | 6/2004 | Rynhart et al. | |
| 2003/0150129 A1 | 8/2003 | Kang et al. | |
| 2003/0220636 A1 * | 11/2003 | Bowman et al. | 606/28 |

FOREIGN PATENT DOCUMENTS

| | | | |
|---|---|---|---|
| DE | 1698221 | 1/1971 | |
| DE | 3904653 A1 | 8/1990 | |
| WO | WO 2005106461 A1 | * 11/2005 | |

OTHER PUBLICATIONS

"AOAC Official Methods of Analysis"; 1995, Fruits and Fruit Products, Chapter 37, pp. 4-5.

* cited by examiner

*Primary Examiner*—Hoai-An D Nguyen
(74) *Attorney, Agent, or Firm*—Townsend and Townsend and Crew LLP; M. Henry Heines

(57) ABSTRACT

The moisture content of a foodstuff or other solid matter is determined by reducing the matter to a paste, packing the paste into a vessel equipped with multiple pairs of plate electrodes and one or more temperature sensors, applying an AC voltage across each pair of electrodes, and measuring the impedance of the paste from each pair of electrodes. The multiple impedance measurements are averaged or otherwise processed to obtain a value that is representative of the paste, and that value and the temperature are processed against calibration data to achieve a value of the moisture content of the paste.

26 Claims, 3 Drawing Sheets

ELECTRONIC MOISTURE TESTER

BACKGROUND OF THE INVENTION

1. Field of the Invention

This invention arises in the area of analytical equipment and instrumentation for the determination of moisture contents in solid materials. This invention is of particular interest in moisture level determinations of foods.

2. Description of the Prior Art

The moisture content of fruits, vegetables, and other foods or commodities is critical for various reasons, both regulatory and practical. The moisture level affects the shelf life, for example, and is a measure of the tendency of particular foods toward spoilage. The moisture level also affects the degree to which certain foods can be processed. In some cases, moisture levels are a factor in consumer preference as well.

Many moisture level determinations in current use operate by passing an electric current or other signal through a sample of the material and measuring the resistance of the material to the current or signal. The resistance generally increases as the moisture level drops. In other methods, infrared spectroscopy is used to measure absorption at a wavelength that is indicative of water content. Still other methods utilize atomic absorption, and further methods use chemical extraction processes.

Many of these methods are of limited accuracy, others are so costly as to be impractical, and some cannot be performed in the environments where testing is needed. One of the causes of inaccuracies is a lack of consistency of the physical properties of the material being tested. Foodstuffs with thick skins, fibrous flesh, or seeds, for example, are difficult to test in their native state due to differences between the water contents of these parts and those of the remainder of the material. When the foodstuffs are processed to prepare for moisture testing, the processing is often performed in an inconsistent manner, thereby introducing variations into the test results.

Prunes and raisins are examples of food materials in which moisture levels are critical. The industry has therefore adopted standardized methods prescribed by the Association of Official Analytical Chemists (AOAC). One such method is "AOAC Official Method 972.20, Moisture in Prunes and Raisins—Moisture Meter Method," published in the *AOAC Official Methods of Analysis* (1995), "Fruits and Fruit Products," Chapter 37, p. 4. This method requires use of a dried fruit analyzer of a specific type, and involves chopping or grinding a sample of the fruit, manually packing the ground fruit into a Bakelite cylinder that is part of the analyzer and that contains a bottom electrode, and doing so in such a way that the ground fruit is tightly packed in the cylinder and particularly around the electrode. A top electrode is then lowered onto the cylinder and pressed into the ground fruit. A thermometer is then inserted into the cylinder. The analyzer is then plugged into an AC outlet and the current adjusted. Readings are taken both from the analyzer and the thermometer. Despite the standardized nature of this method, significant human error is introduced into the readings since so much of the procedure is performed by hand. The manual filling of the cylinder, for example, as well as the manual compression of the sample around the electrodes, are difficult to duplicate to any degree of precision. Confirmation of the test results from different operators by more accurate but tedious vacuum oven determinations has shown that samples with the same moisture level can produce results by this method that vary by as much as 8%.

Another method prescribed by the AOAC is "AOAC Official Method 934.06, Moisture in Dried Fruits," likewise published in the *AOAC Official Methods of Analysis* (1995), "Fruits and Fruit Products," Chapter 37, p. 4. According to this method, a 5-10 g portion of a prepared sample is spread over the bottom of a metal dish, and the sample is then dried on the dish for 6 hours at 70° C. at reduced pressure under a flowing atmosphere of air that has been dried by bubbling through sulfuric acid. The dish is then covered, cooled and weighed. When raisins are tested by this method, the procedure requires the sample of raisins to be mixed with finely divided asbestos, then the mixture evaporated on a steam bath. It should be evident from this description that the entire procedure is replete with opportunities for operator error.

SUMMARY OF THE INVENTION

The present invention resides in a process and apparatus for moisture level determinations of foodstuffs and other solid matter in a manner that reduces or eliminates many of the shortcomings and inaccuracies of the prior art. A common feature of the process and apparatus is their use of multiple impedance measurements of the material to be tested, each measurement taken at a different location within a body of the material once the material has been homogenized into, i.e., converted to, a paste. Temperature measurements of the material are also taken. The impedance reflects both the electrical resistivity and dielectric constant of the material, both of which vary with the moisture content and the temperature. The impedance is determined by applying an alternating electrical potential at a selected frequency, thereby enabling the measurement to be compared with calibrated standards. Signals representing each impedance measurement are generated, and these signals and the temperature measurements are processed collectively by a data processor that compares them to calibration data that correlates the signals with known moisture levels. The comparison thus results in a determination of the moisture level of the paste, and hence the starting material, from multiple measurements at different locations in the same sample of paste after preparation of the paste under controlled conditions. In preferred embodiments, the paste is prepared by automated equipment operated under controlled and reproducible conditions, and the paste immediately upon formation is placed in the vessel where impedance and temperature measurements are taken. Operator handling of the material to be tested is thus minimized and can be eliminated entirely during both paste formation and impedance measurement. A preferred vessel is an elongated tube with electrode pairs inside the tube and spaced along its length, and one or more temperature sensors arranged to detect the temperature of matter contained in the interior of the tube.

Other features, objects, and advantages of the invention will be apparent from the description below.

DETAILED DESCRIPTION OF THE INVENTION AND PREFERRED EMBODIMENTS

The process and apparatus of this invention are useful in performing moisture level determinations of any solid matter that requires or will benefit from knowledge of its moisture level. Foodstuffs are prime examples of such matter, and particularly dried fruits and vegetables. Any such matter that can be homogenized into a paste can be tested by the present invention. The term "paste" is used herein to denote any mash, slurry, or puree, or any form that is otherwise flowable or can be densely packed to uniform pressure. For fruits, vegetables, meats, and dried forms of these foodstuffs, these pastes can be prepared by conventional food processing equipment, such as meat grinders, blenders, and food processors. The paste is preferably formed without any additives, and particularly without any added moisture, so that the moisture content of the paste is the same as that of the starting foodstuff material.

Figure 1:
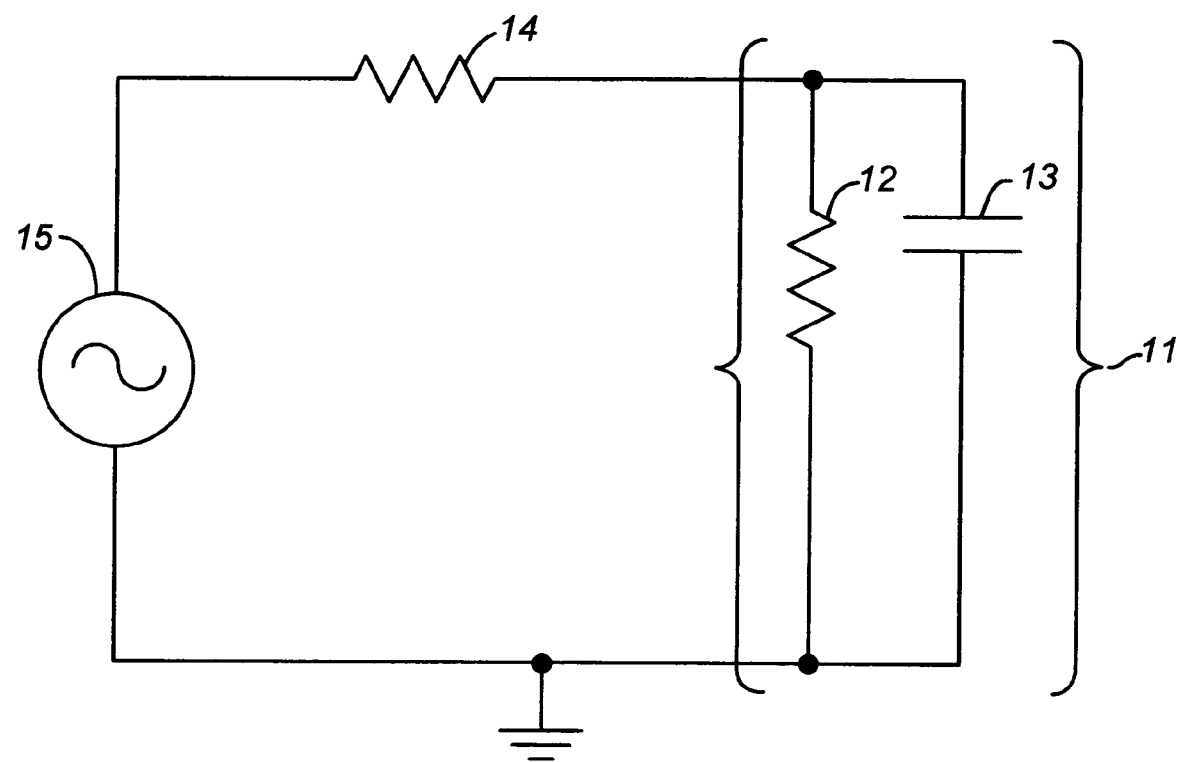
FIG. 1 is a diagram of an electrical circuit used for modeling the material as a parallel reactive load that exhibits a characteristic impedance signal in accordance with this invention.

Moisture levels are determined from multiple measurements of electrical impedance in the paste. The electrical impedance is determined by connecting the paste to an electrical circuit in such a manner that the formation of a parallel reactive load is completed by the paste, i.e., a load that exhibits a characteristic impedance value that varies with the frequency of an AC voltage when such a voltage is applied across the paste. The parallel reactive load is formed by connecting the paste between a source resistance and a ground via a set of parallel electrodes as shown in FIG. 1, modeling the paste 11 as both a resistor 12 and a capacitor 13 in parallel with each other in the circuit, while both the resistor and the capacitor are connected in series with the source resistance 14. When the AC voltage 15 is applied across the load, the ratio of the AC voltage across the load 11 to the AC voltage at the source resistance 14 is measured and the ratio is used in calculating the impedance at a given AC frequency.

The vessel in which the measurements are made is of fixed or predetermined dimensions, notably the spacing between the walls of the vessel and hence the electrodes and the cross sectional area across which the voltage is applied. As a result, the resistance is directly proportional to the electrical resistivity. Likewise, the electrodes of each electrode pair across which the voltage is applied are of fixed or predetermined surface area and separation, with the result that the parallel plate capacitance is directly proportional to the dielectric constant of the paste. Since electrical resistivity and dielectric constant both vary with moisture content, the use of a known frequency and the determination of the temperature of the paste at the time that the impedance measurements are taken cause the combination of impedance and temperature measurements to be a direct indication of the moisture level of the paste.

The conversion of these measurements to a moisture level is achieved by a relationship determined by calibration data, i.e., corresponding measurements made by the device and derived from pastes of the same matter but of known moisture levels. The known moisture levels can be determined by any conventional but accurate means of moisture determination. Examples of these methods are vacuum drying methods, of which the AOAC methods referenced above are examples, although it is preferred that the calibration data be the result of multiple readings for any given method and that an appropriate statistical method be applied to the multiple readings to achieve a value of high reliability. Vacuum oven drying methods in general are well known to those skilled in the art of food processing methods. A sufficient number of paste samples with differing moisture levels will be used to establish a data set or calibration curve that spans the desired range. Multiple curves will be appropriate in certain cases where the potential range of sample moisture levels is particularly broad. A preferred relation is a three-dimensional plot in which moisture level is plotted as a function of both impedance and temperature.

With multiple impedance measurements, any of the wide variety of known statistical treatments can be applied to generate a value that is indicative of the paste sample as a whole. Abnormalities, aberrations, or other deviations from a general trend of detected values are eliminated in certain treatments and the remaining values can be averaged, either as a geometrical mean or an arithmetic mean, or a median value taken. In a presently preferred method, the highest and lowest values are eliminated through statistical outlier tests, and the remainder are averaged by an arithmetic mean. This type of data processing, together with a comparison of the results with calibration data in a standardized plot, are readily performed by simple software that is readily familiar to those skilled in the art.

The number of impedance measurements is not critical to the invention and can vary widely, with optimum numbers possibly varying with the particular material whose moisture level is to be determined. In most cases, best results will be achieved with from 5 to 100 measurements at different locations within the paste, and preferably from 10 to 60 measurements. Plate electrodes are preferably used, and the gap width, i.e., the spacing between the electrodes of any single pair, may vary. A uniform gap width among all electrode pairs is preferred. In most cases, best results will be obtained with a gap width of from about 0.3 inch (0.76 cm) to about 3 inches (7.6 cm), preferably from about 0.5 inch (1.3 cm) to about 2 inches (5.1 cm). A presently preferred gap width is about 1.0 inch (2.54 cm). The surface area of each plate electrode can likewise vary, although best results are generally obtained with a surface area of from about 0.03 in$^2$ (0.19 cm$^2$) to about 0.3 in$^2$ (1.9 cm$^2$). A presently preferred surface area is about 0.09 in$^2$ (0.6 cm$^2$).

The alternating voltage can be supplied by any conventional AC power supply. The voltage can assume any waveform that can be used for an impedance measurement. A sine wave is particularly convenient and therefore preferred. Both the voltage and the frequency can vary and are not critical to the invention, although optimal values will vary with the material being tested. A preferred range for the maximum voltage is from about 1 mV to about 100 V, with a range of from about 0.1 V to about 50 V more preferred, and from about 0.3 V to about 30 V the most preferred. Preferred frequencies are those within the range of from about 60 Hz to about 200 kHz, with a range of from about 300 Hz to about 30 kHz the most preferred. In a presently preferred embodiment, the maximum voltage is 5 V and the frequency is 1 kHz in a sine wave.

The impedance measurements can be performed while the paste is in motion, such as flowing or being forced through a conduit, or while the paste is stationary, and the multiple measurements can be taken simultaneously or in succession. In a presently preferred embodiment, the measurements are taken in a static paste and in succession so that voltage is applied across only one pair of electrodes at a time.

Temperature measurements can be made by any conventional means, preferably in the paste itself while inside the vessel where the impedance measurements are being taken. Any conventional temperature sensor can be used that emits a signal capable of being processed. Examples are thermocouples, thermistors, metallic resistive temperature devices (RTDs), infrared sensors, bimetallic devices, fluid-expansion devices, and change-of-state temperature sensors. Thermistors are presently preferred. The number and location of the temperature sensors can vary and are not critical to the invention. Preferably, two or more sensors are used.

A convenient shape for the vessel in which the impedance and temperature are measured is that of an elongated conduit, i.e., either a tube or pipe, and preferably of uniform cross section over the length in which the measurements are to be taken. The conduit will have a longitudinal axis, and the electrode pairs preferably consist of plate electrodes spaced apart along the axis, most conveniently at regular intervals. The two plates of each pair of electrodes are preferably positioned on opposite sides of the axis, directly facing each other. The spacing between the centers of adjacent pairs can vary widely. A preferred spacing is from about 0.2 inch (0.5 cm) to about 2.0 inches (5.1 cm). In a presently preferred embodiment, the center-to-center spacing is 0.375 inch (0.95 cm). The volume of the vessel, and hence the volume of the paste being measured, may vary as well, and in preferred embodiments will range from about 3 to about 3,000 cm$^3$, or most preferably from about 10 to about 1,000 cm$^3$.

Figure 2:
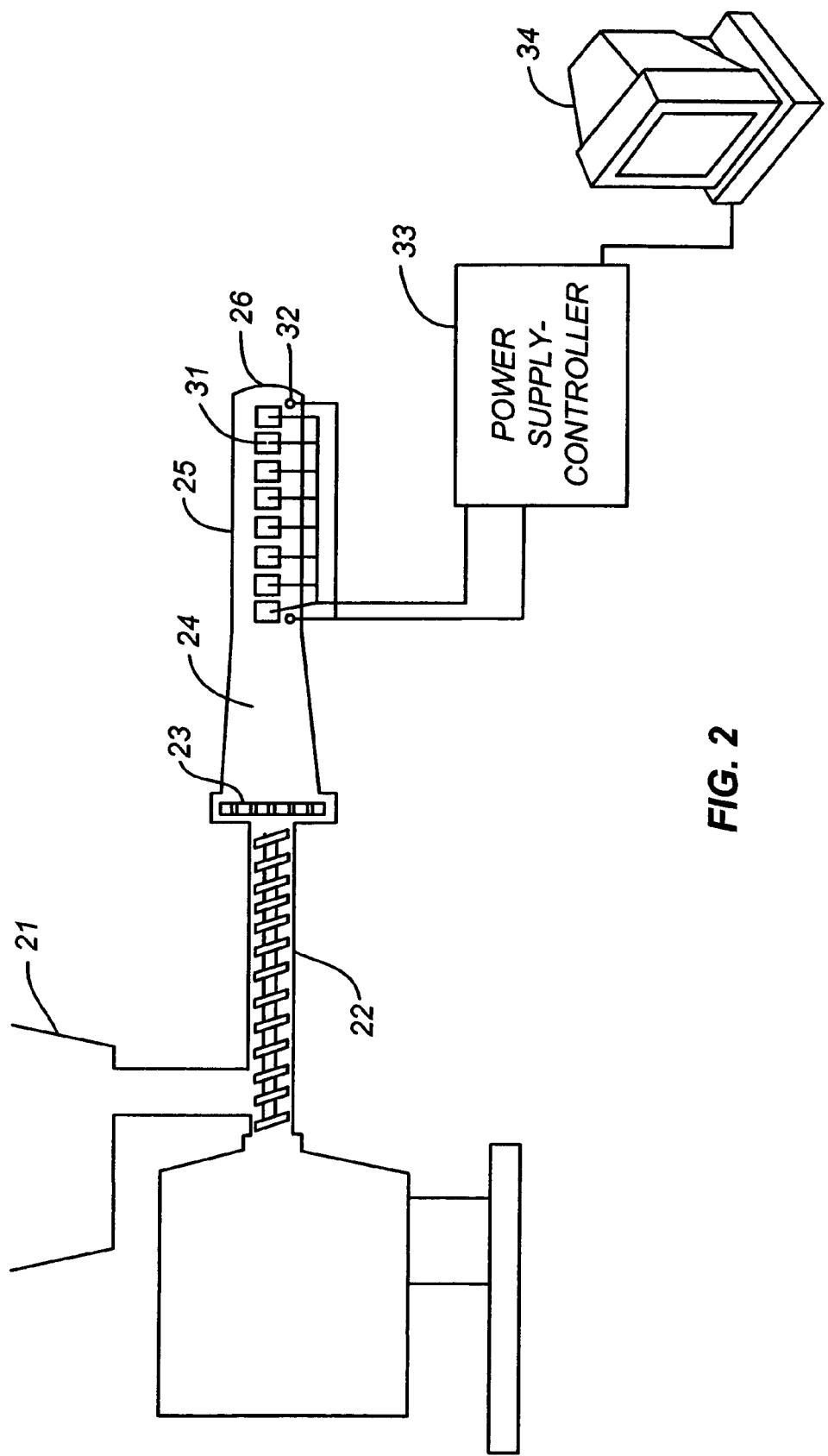
FIG. 2 is a schematic of a moisture determination apparatus in accordance with the present invention.
Figure 3:
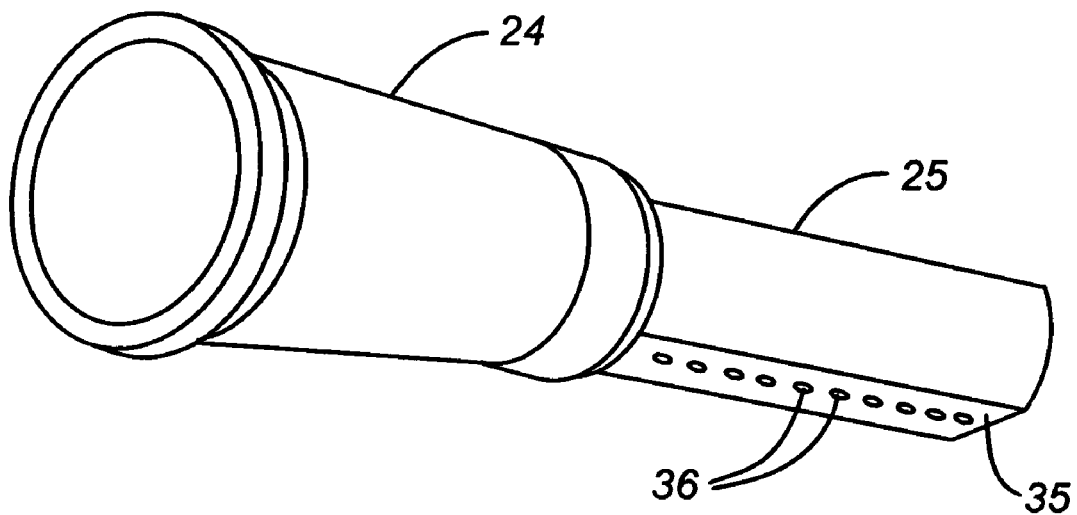
FIG. 3 is a perspective view of one component of the apparatus of FIG. 2.
Figure 4:
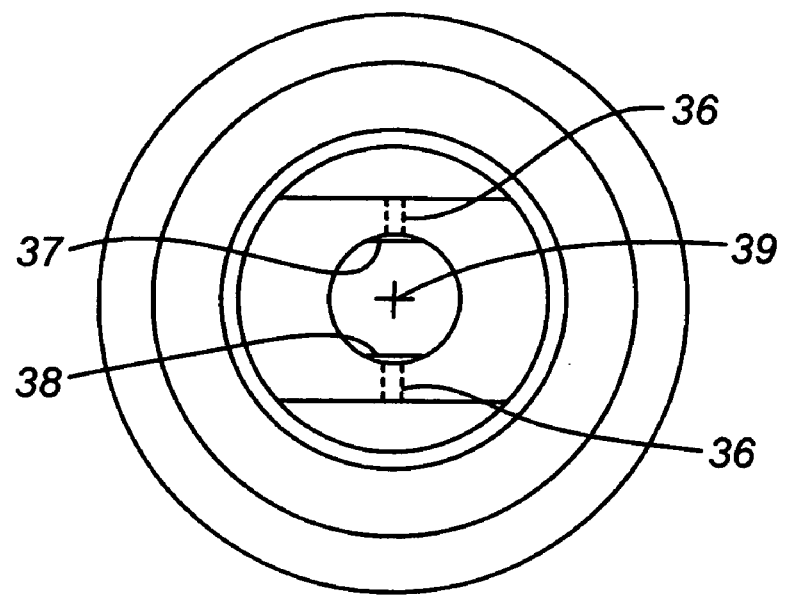
FIG. 4 is an end view of the component of FIG. 3.

While the apparatus of this invention is susceptible to a wide range of configurations, an understanding of the critical features of the invention as applied to all embodiments will be gained from an explanation of one particular embodiment. FIGS. 2, 3, and 4 hereto illustrate one such embodiment.

In the schematic diagram of FIG. 2, material to be tested, such as dried fruit, is placed in a hopper 21 from which it is fed to a grinder 22 and forced through a perforated plate 23. The paste emerging from the plate enters a funnel 24 and passes from there to a tube 25, which is the elongated vessel in which the impedance measurements are taken. The grinder 22 applies sufficient force to the paste to fully pack the paste inside the tube, and once the tube is filled with the paste, the grinder is halted and the paste is allowed to rest motionless in the tube. The tube can be open or vented at its distal end 26 as it is being filled, and capped after the tube is fully packed. Plate electrodes 31 inside the tube contact the paste, and thermistors 32 sense the temperature of the paste. A power supply and controller 33 supplies voltage to the electrodes 31 and receives both impedance signals and temperature signals from the electrodes and thermistors. The signals are processed in an embedded microcontroller 34 which calculates the moisture level from the signals and displays the results.

A perspective view of the funnel 24 and tube 25 from below without the electrical or thermistor connections appears in FIG. 3. The tube has two flat sides, of which only one 35 is visible, and both flat sides are penetrated by a series of ports 36 in which are inserted the electric leads for the electrode plates and for the thermistors.

FIG. 4 is an end view of the funnel and tube from the funnel end, showing the interior 37 of the tube, i.e., the space that will be occupied by the paste. Plate electrodes 37, 38 on opposite sides of the tube axis 39 form one electrode pair.

The foregoing is offered primarily for purposes of illustration and is not intended to limit the scope of the invention. Further variations in the procedural steps, operating conditions, system components, configurations and arrangements will be readily apparent to those skilled in the art and can be made without departing from the spirit and scope of the invention.

What is claimed is:

1. A process for determining moisture content in solid matter, said process comprising:
    (a) reducing said solid matter to a paste;
    (b) placing said paste in an elongated vessel having a longitudinal axis, said vessel containing a plurality of independent pairs of electrodes positioned at a plurality of locations along said axis, the electrodes of any single pair directly opposing each other across said axis;
    (c) imposing an alternating voltage at a selected frequency across each of said pairs of electrodes and through said paste, determining an electrical impedance value across each of said pairs arising from said alternating voltage, and generating a signal representative of each of said values;
    (d) detecting the temperature of said paste in said elongated vessel; and
    (e) compiling test data from said signals and said temperature, and comparing said test data so compiled to calibration values correlating said test data with moisture levels, thereby determining said moisture content of said solid matter.

2. The process of claim 1 wherein the electrodes of any single pair are separated by a gap, and the gaps of all said pairs are of equal width.

3. The process of claim 1 wherein said elongated vessel contains from 5 to 100 pairs of electrodes.

4. The process of claim 1 wherein said elongated vessel contains from 10 to 60 pairs of electrodes.

5. The process of claim 1 wherein said alternating voltage has a maximum voltage ranging from about 1 mV to about 100 V.

6. The process of claim 1 wherein said alternating voltage has a maximum voltage ranging from about 0.1 V to about 50 V.

7. The process of claim 1 wherein said alternating voltage has a maximum voltage ranging from about 0.3 V to about 30 V.

8. The process of claim 1 wherein said selected frequency is from about 60 Hz to about 200 kHz.

9. The process of claim 1 wherein said selected frequency is from about 300 Hz to about 30 kHz.

10. The process of claim 1 wherein step (a) comprises forcing said solid matter through a perforated plate.

11. The process of claim 1 wherein step (b) comprises placing from about 3 to about 3,000 cm$^3$ of said paste in said elongated vessel.

12. The process of claim 1 wherein step (b) comprises placing from about 10 to about 1,000 cm$^3$ of said paste in said elongated vessel.

13. The process of claim 1 wherein step (d) is performed by at least one thermistor within said vessel.

14. The process of claim 1 wherein step (d) is performed by a plurality of thermistors within said vessel.

15. The process of claim 1 wherein step (e) comprises averaging a plurality of said signals to yield an average signal value and comparing said average signal value and said temperature to values represented on a three-dimensional calibration data curve in which moisture level is plotted as a function of both impedance and temperature.

16. An apparatus for determining moisture content in a paste, said apparatus comprising:
    an elongated vessel for receiving said paste, having a longitudinal axis and containing a plurality of independent pairs of electrodes positioned at a plurality of locations along said axis, the electrodes of any single pair directly opposing each other across said axis;
    means for imposing an alternating voltage at a selected frequency across each of said pairs of electrodes when said vessel is filled with said paste and for detecting electrical impedance across each of said pairs and through said paste and for correlating said electrical impedance with moisture content; and means for detecting the temperature of the interior of said vessel.

17. The apparatus of claim 16 wherein said elongated vessel is of uniform cross section and the electrodes of any single pair are separated by a gap, the gaps of all said pairs being of equal width.

18. The apparatus of claim 16 comprising from 5 to 100 pairs of said electrodes.

19. The apparatus of claim 16 wherein comprising from 10 to 60 pairs of electrode.

20. The apparatus of claim 16 wherein said means for detecting the temperature of the interior of said vessel are comprised of at least one thermistor.

21. The apparatus of claim 16 wherein said means for detecting the temperature of the interior of said vessel are comprised of a plurality of thermistors.

22. The apparatus of claim 16 further comprising means for reducing solid matter to a paste.

23. The apparatus of claim 22 wherein said means for reducing solid matter to a paste is a drive means arranged to force said solid matter through a perforated plate.

24. The apparatus of claim 16 in which said elongated vessel has an internal capacity of from about 3 to about 3,000 $cm^3$.

25. The apparatus of claim 16 in which said elongated vessel has an internal capacity of from about 10 to about 1,000 $cm^3$.

26. The apparatus of claim 16 in which said elongated vessel is an elongated tube.

* * * * *